(12) United States Patent
Lee et al.

(10) Patent No.: US 9,867,704 B2
(45) Date of Patent: Jan. 16, 2018

(54) CARDIAC VALVE FIXING DEVICE

(71) Applicants: PUSAN NATIONAL UNIVERSITY INDUSTRY-UNIVERSITY COOPERATION FOUNDATION, Busan (KR); S&G BIOTECH, INC., Gyeonggi-do (KR)

(72) Inventors: Han Cheol Lee, Busan (KR); Sung Kwon Kang, Gyeonggi-do (KR); Seung Hwan Jegal, Seoul (KR); Ui Soo Jang, Gyeonggi-do (KR)

(73) Assignees: PUSAN NATIONAL UNIVERSITY INDUSTRY-UNIVERSITY COOPERATION FOUNDATION, Busan (KR); S&G BIOTECH, INC., Gyeonggi-Do (KR)

( * ) Notice: Subject to any disclaimer, the term of this patent is extended or adjusted under 35 U.S.C. 154(b) by 11 days.

(21) Appl. No.: 14/889,739

(22) PCT Filed: Apr. 16, 2014

(86) PCT No.: PCT/KR2014/003312
§ 371 (c)(1),
(2) Date: Nov. 6, 2015

(87) PCT Pub. No.: WO2014/181975
PCT Pub. Date: Nov. 13, 2014

(65) Prior Publication Data
US 2016/0089233 A1 Mar. 31, 2016

(30) Foreign Application Priority Data
May 6, 2013 (KR) .................. 10-2013-0050795

(51) Int. Cl.
*A61F 2/24* (2006.01)
*A61B 17/064* (2006.01)
*A61B 17/00* (2006.01)

(52) U.S. Cl.
CPC ........ *A61F 2/246* (2013.01); *A61B 17/00234* (2013.01); *A61B 17/0644* (2013.01); *A61F 2/2466* (2013.01); *A61B 2017/00243* (2013.01); *A61B 2017/00783* (2013.01); *A61B 2017/0641* (2013.01); *A61B 2017/0645* (2013.01)

(58) Field of Classification Search
CPC ......... A61F 2/24; A61F 2/2403; A61F 2/2412
USPC .................................. 623/2.1–2.19
See application file for complete search history.

(56) References Cited

U.S. PATENT DOCUMENTS

| | | | | |
|---|---|---|---|---|
| 6,730,121 B2* | 5/2004 | Ortiz | ............ | A61F 2/2409 623/2.14 |
| 6,964,684 B2* | 11/2005 | Ortiz | ............ | A61F 2/2409 623/2.11 |
| 6,974,476 B2* | 12/2005 | McGuckin, Jr. | ...... | A61F 2/2412 623/2.11 |
| 7,578,843 B2* | 8/2009 | Shu | ............ | A61F 2/2409 623/2.11 |
| 7,753,922 B2* | 7/2010 | Starksen | ............ | A61F 2/2445 227/175.1 |
| 9,023,098 B2* | 5/2015 | Kuehn | ............ | A61F 2/2412 623/1.11 |
| 9,066,799 B2* | 6/2015 | Seguin | ............ | A61F 2/2418 |
| 9,125,738 B2* | 9/2015 | Figulla | ............ | A61F 2/2412 |
| 2003/0023303 A1 | 1/2003 | Palmaz et al. | | |
| 2003/0040792 A1* | 2/2003 | Gabbay | ............ | A61F 2/2418 623/2.11 |
| 2004/0088047 A1* | 5/2004 | Spence | ............ | A61F 2/2412 623/2.36 |
| 2005/0288786 A1* | 12/2005 | Chanduszko | ...... | A61B 17/0057 623/11.11 |
| 2006/0167543 A1* | 7/2006 | Bailey | ............ | A61F 2/2418 623/2.18 |
| 2012/0095552 A1* | 4/2012 | Spence | ............ | A61F 2/2412 623/2.36 |
| 2013/0304197 A1* | 11/2013 | Buchbinder | .......... | A61F 2/2427 623/2.11 |
| 2014/0005778 A1* | 1/2014 | Buchbinder | .......... | A61F 2/2445 623/2.18 |
| 2014/0163672 A1* | 6/2014 | Seguin | ............ | A61F 2/2409 623/2.38 |
| 2014/0180401 A1* | 6/2014 | Quill | ............ | A61F 2/2418 623/2.17 |
| 2014/0222136 A1* | 8/2014 | Geist | ............ | A61F 2/2466 623/2.11 |
| 2015/0005874 A1* | 1/2015 | Vidlund | ............ | A61F 2/2418 623/2.14 |
| 2015/0351904 A1* | 12/2015 | Cooper | ............ | A61F 2/2418 623/2.1 |
| 2015/0366667 A1* | 12/2015 | Bailey | ............ | A61F 2/2418 623/2.11 |
| 2016/0089233 A1* | 3/2016 | Lee | ............ | A61B 17/0644 623/2.1 |
| 2016/0158001 A1* | 6/2016 | Wallace | ............ | A61F 2/2409 623/2.18 |
| 2016/0199182 A1* | 7/2016 | Gorman, III | .......... | A61F 2/2418 623/2.18 |
| 2016/0338826 A1* | 11/2016 | Chau | ............ | A61F 2/2418 |

FOREIGN PATENT DOCUMENTS

| | | |
|---|---|---|
| KR | 20100124296 | 11/2010 |
| KR | 20110038617 | 4/2011 |
| KR | 20120100180 | 9/2012 |

* cited by examiner

*Primary Examiner* — Suzette J Gherbi
(74) *Attorney, Agent, or Firm* — Workman Nydegger

(57) ABSTRACT

A cardiac valve fixing device of the present invention comprises: a first structure, which continuously comes into contact with the lower surface of at least one cardiac valve; a second structure, which is connected to the first structure and continuously comes into contact with the upper surface of the cardiac valve; and a fixing barb, which is equipped in at least one of the first structure and the second structure and protrusively formed to the direction of the cardiac valve so as to be inserted into the cardiac valve. Accordingly, the cardiac valve fixing device of the present invention stably fixes the cardiac valve.

15 Claims, 11 Drawing Sheets

[Fig. 1]
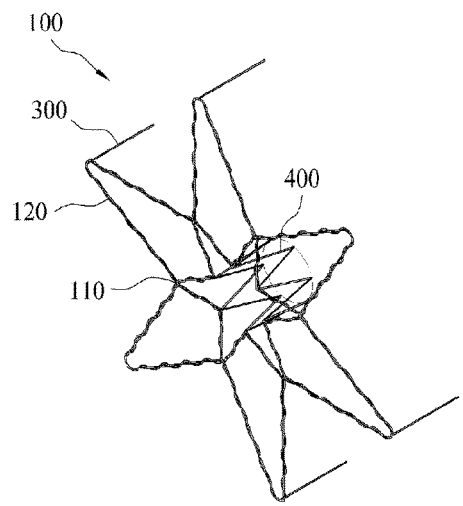
[Fig. 2]
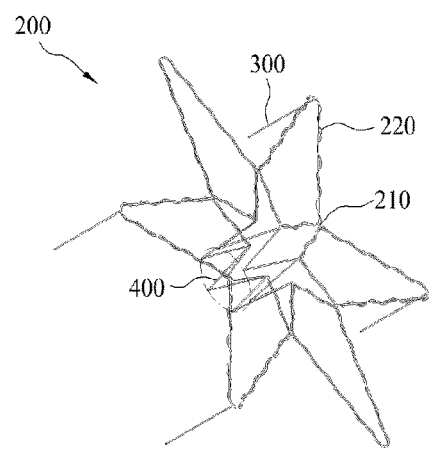
[Fig. 3]
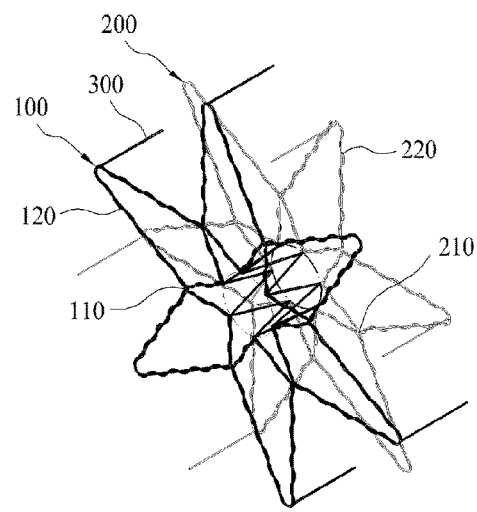

[Fig. 4]
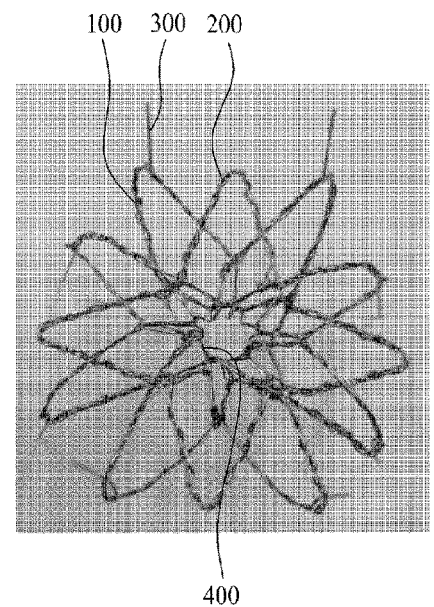
[Fig. 5]
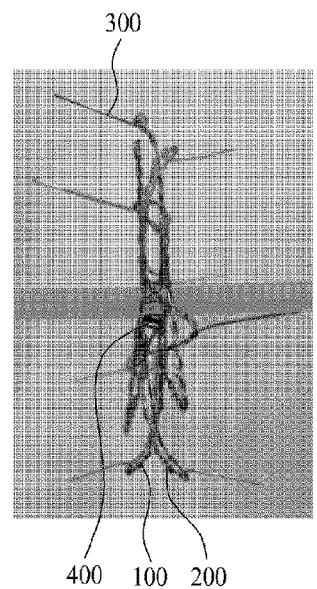
[Fig. 6]
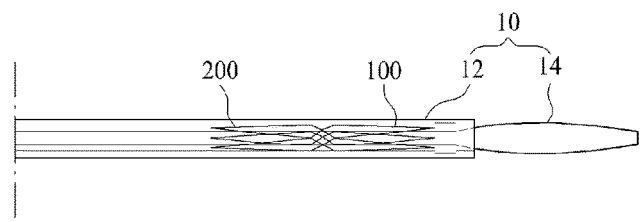

[Fig. 7]
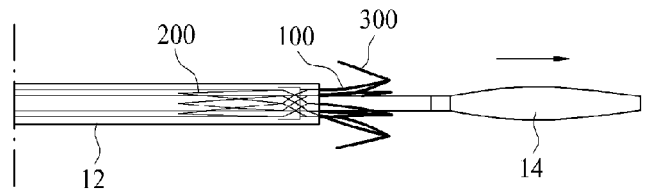
[Fig. 8]
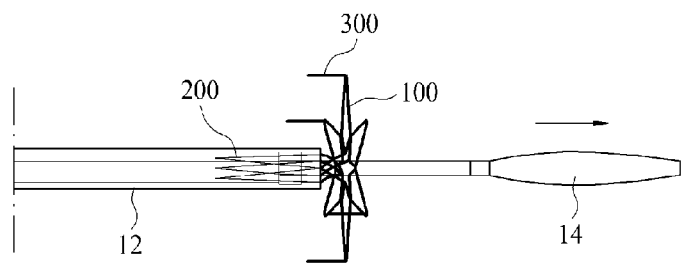
[Fig. 9]
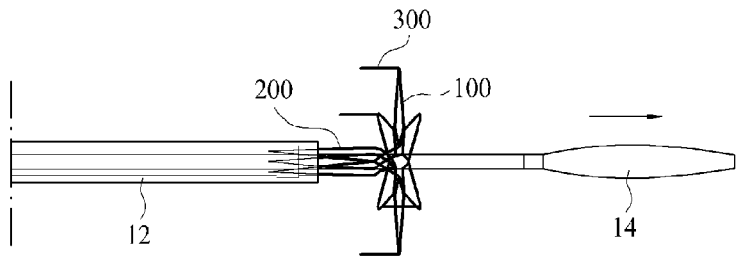
[Fig. 10]
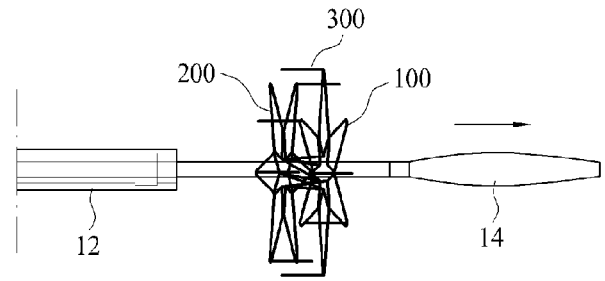

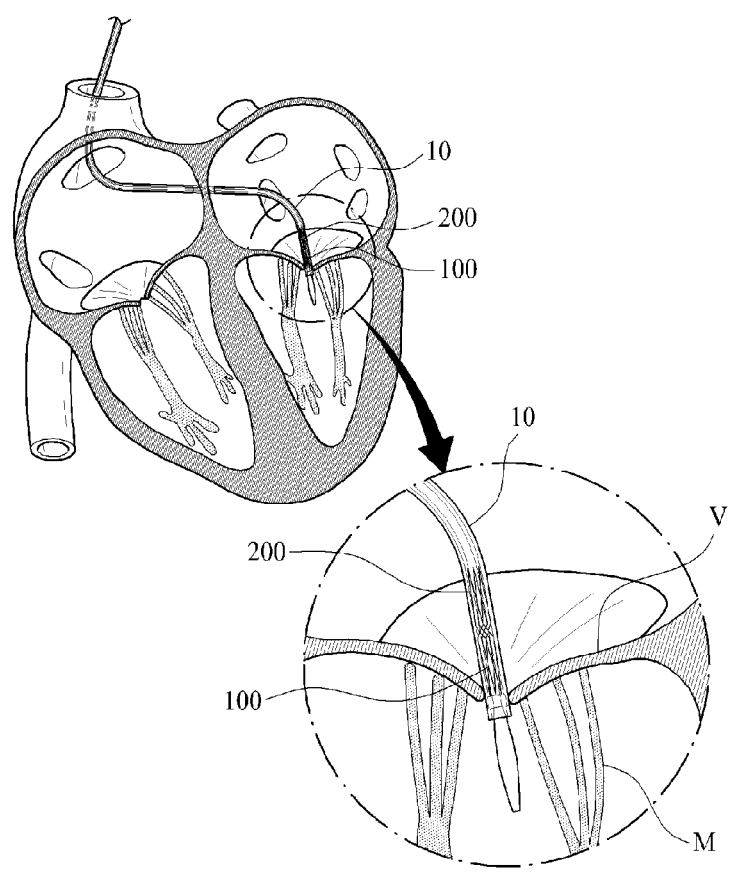
[Fig. 11]

[Fig. 12]
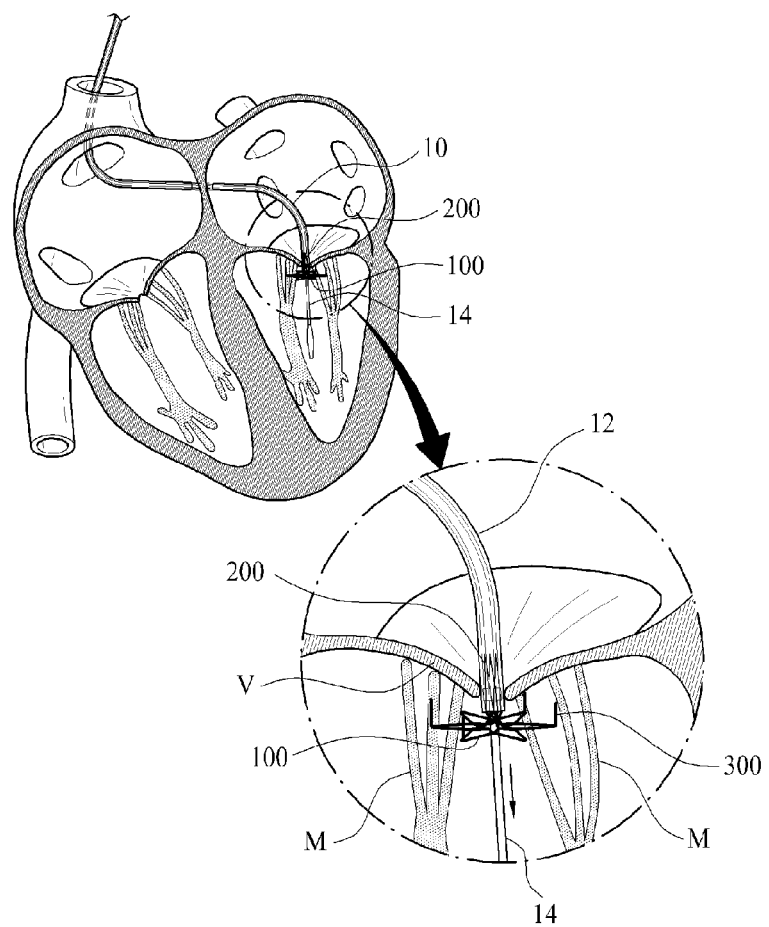

[Fig. 13]
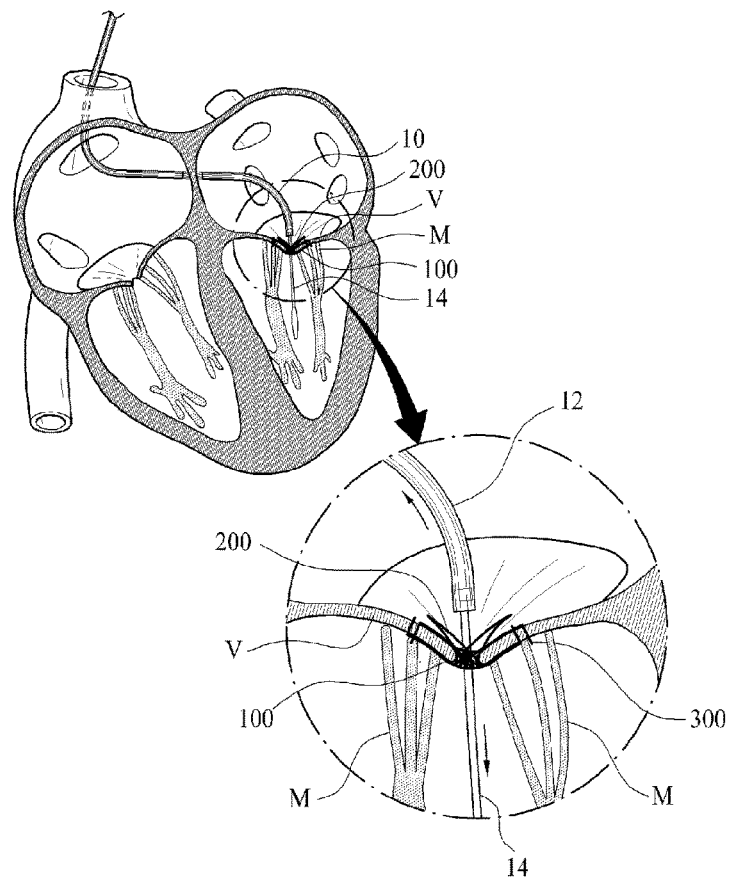
[Fig. 14]
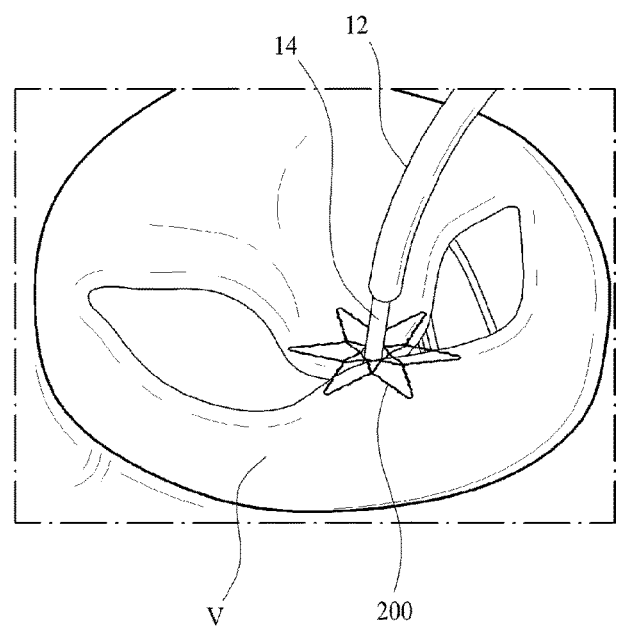

[Fig. 15]
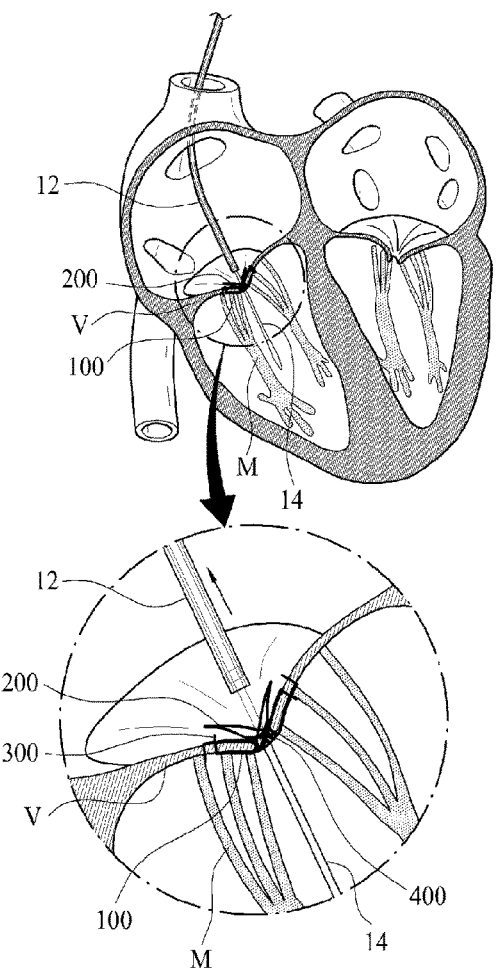
[Fig. 16]
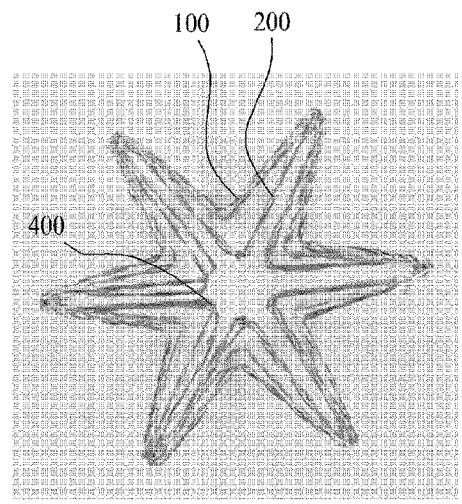

[Fig. 17]
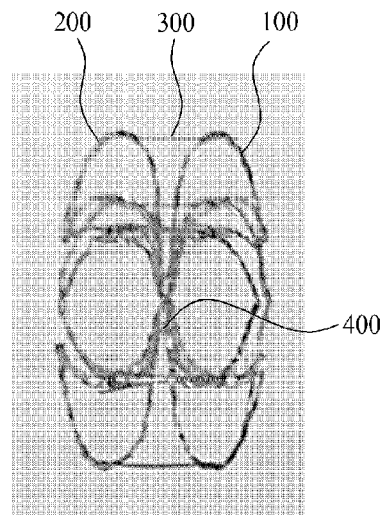
[Fig. 18]
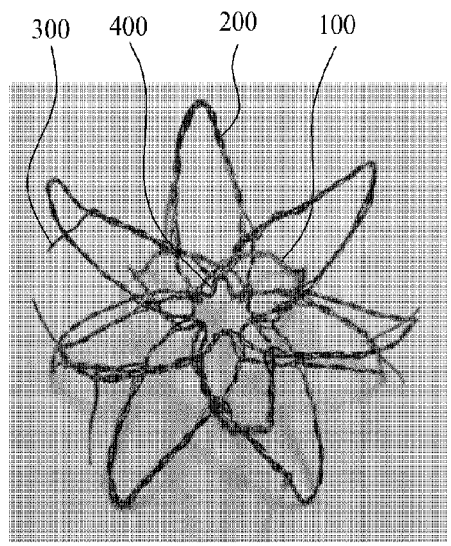

[Fig. 19]
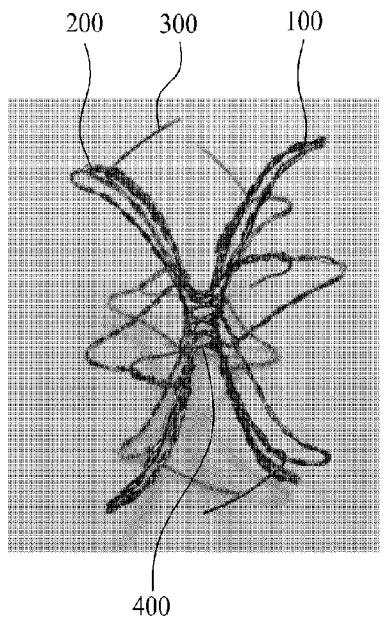
[Fig. 20]
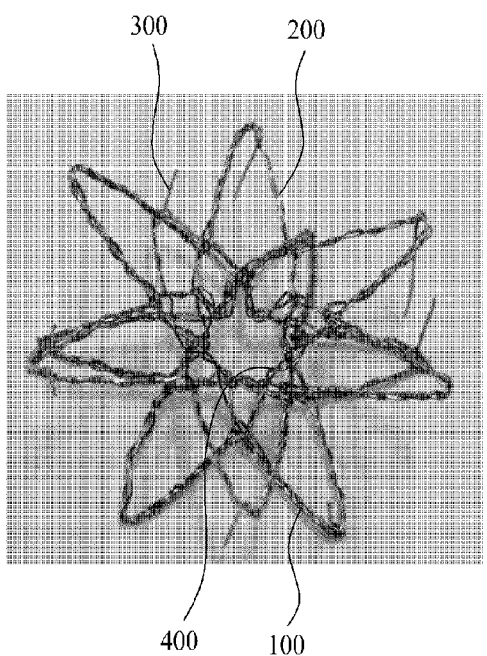

[Fig. 21]
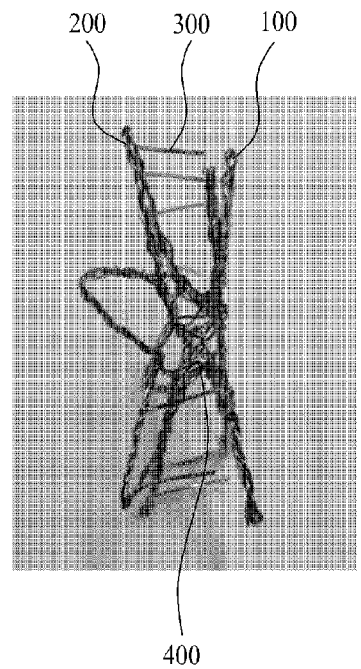
[Fig. 22]
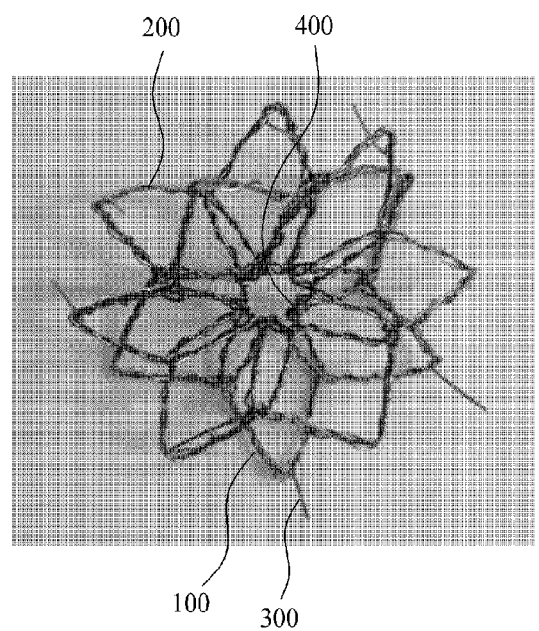

[Fig. 23]
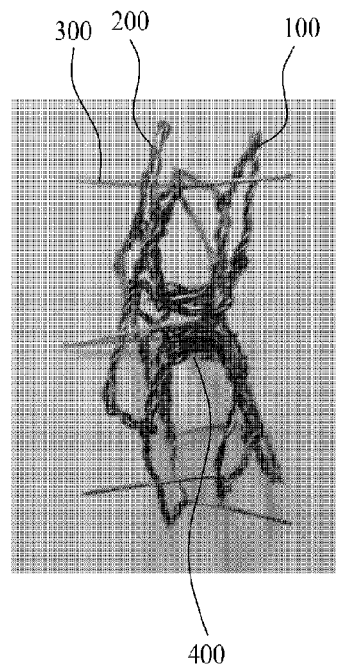

CARDIAC VALVE FIXING DEVICE

TECHNICAL FIELD

The present invention relates to a cardiac valve fixing device, and more particularly, to a cardiac valve fixing device that fixes a cardiac valve by being inserted into the heart.

BACKGROUND ART

In general, recently, various kinds of treatment of inserting a separate structure into the inside of a patient's body using an endoscope device, without performing laparotomy of the patient's body have been performed.

For example, various types of treatment, such as extending the blood vessel by performing a stent treatment on a user's blood vessel, or fixing a particular site by inserting a separate, have been performed.

Recently, there has been an attempt of a treatment that prevents the backflow of blood by inserting a separate fixing device to the patient's heart such that the patient's cardiac valve are stably opened and closed. In particular, when the cardiac valve is not fully closed, a symptom of backflow of blood occurs, and thus, at the time of excessive exercise, a difficulty in breathing occurs, or atrial fibrillation may occur.

In order to solve such problems, a cardiac valve fixing device which fixes the cardiac valve by inserting a separate fixing device to the inside of the heart has been developed. Considering the conventionally developed cardiac valve fixing device, after insertion into the patient's heart using the insertion device, the device comes into contact with the upper and lower surfaces of the cardiac valve to fix the cardiac valve of the target site, thereby easily allowing the opening and closing of the cardiac valve.

However, when simply fixing the cardiac valve in a form of being pressed in contact with the cardiac valve of a patient, a problem of being easily separated by the continually moving cardiac valve occurs. Since this problem exerts vital effects on the patient's body, there is a problem of a need for being urgently solved.

Further, in the case of cardiac valve, since there is a muscle fiber that moves, there has been also a problem of an occurrence of interference between the cardiac valve fixing device and the muscle fiber.

DISCLOSURE

Technical Problem

An embodiment of the present invention is directed to provide a cardiac valve fixing device which is capable of stably fixing the cardiac valve without being separated by coming into contact with the upper and lower surfaces of a cardiac valve of a target user.

Further, another embodiment of the present invention is directed to provide a cardiac valve fixing device which can stably fix the cardiac valve without interference with the valve muscle fibers connected to the cardiac valve when fixing the cardiac valve.

Technical Solution

According to an aspect of the present invention, there is provided a cardiac valve fixing device that includes a first structure that continuously comes into contact with lower surfaces of one or more the cardiac valves, a second structure that is connected to the first structure and continuously comes into contact with upper surfaces of the cardiac valves, and a fixing barb that is provided in at least one of the first structure or the second structure, is formed to protrude in a direction of the cardiac valve, and is inserted into the cardiac valves.

Furthermore, the fixing barb may be formed on the outside along the periphery of the first structure or the second structure.

The first structure may a predetermined periphery, and a part along the periphery may be formed with a first recessed portion recessed inward.

The second structure may have a predetermined periphery, and a part along the periphery may be formed with a second recessed portion recessed inward.

The first structure may have a predetermined periphery, and a part along the periphery is formed with a first recessed portion recessed inward, the second structure may have a predetermined periphery, and a apart along the periphery may be formed with a second recessed portion recessed inward, and the first recessed portion and the second recessed portion may disposed to intersect with each other.

The fixing barb may be formed only in one of mutually facing points of the first structure and the second structure.

The second structure may be formed to have a shape different from the first structure.

Also, the device may further include a connecting portion that is disposed between the first structure and the second structure, has a periphery of a relatively small size, and connects the first structure and the second structure.

It should be understood that different embodiments of the invention, including those described under different aspects of the invention, are meant to be generally applicable to all aspects of the invention. Any embodiment may be combined with any other embodiment unless inappropriate. All examples are illustrative and non-limiting.

Advantageous Effects

According to the cardiac valve fixing device of the present invention having the above-described configuration has the following effects.

First, there is an advantage of being able to fix the cardiac valve so as not to be separated by enhancing the adhesive strength with the cardiac valve, by including a separate fixing barb that is inserted into the cardiac valve on the first structure and the second structure fixed while being in contact with the upper and lower surfaces of the cardiac valve.

Second, there is an advantage of being able to stably maintain a fixed state of the first structure, by increasing a contact area with the heat valve due to an increase in length of periphery as the first structure and the second structure are formed to be recessed inward.

Third, there is an advantage of being able to preventing an occurrence of the interference between the first structure and valve tissue fiber, by provision of the first recessed portion recessed inward along the periphery of the first structure coming into contact with the lower surface of the cardiac valve and by arrangement of the valve fiber tissue connected to the cardiac valve.

The effects of the present invention are not limited to the above-described effects, and other effects not mentioned will be clearly understood from the scope of the claims to those skilled in the art.

BRIEF DESCRIPTION OF THE DRAWINGS

FIG. 1 is a perspective view schematically showing a configuration of a first structure in a cardiac valve fixing device according to an embodiment of the present invention.

FIG. 2 is a perspective view schematically showing a construction of a second structure in the cardiac valve fixing device according to an embodiment of the present invention.

FIG. 3 is a real view showing a state in which the first structure and the second structure are coupled to each other in the cardiac valve fixing device according to an embodiment of the present invention.

FIG. 4 is a real view showing a state in which the first structure and the second structure are coupled to each other in the cardiac valve fixing device according to an embodiment of the present invention.

FIG. 5 is a real view showing a side surface of FIG. 4.

FIGS. 6 to 8 are diagrams showing a state in which the first structure in the cardiac valve fixing device of FIG. 1 is exposed, while having shape by a separate insertion device.

FIGS. 9 and 10 are diagrams showing a state in which the second structure in the cardiac valve fixing device of FIG. 5 is exposed, while having shape by an insertion device.

FIG. 11 is a perspective view showing a state in which the cardiac valve fixing device according to an embodiment of the present invention is moved into the inside of the heart by a separate insertion device.

FIG. 12 is a diagram showing a state in which the first structure is in contact with a lower surface of a mitral valve in the cardiac valve fixing device according to an embodiment of the present invention.

FIG. 13 is a diagram showing a state in which the second structure is in contact with an upper surface of the mitral valve in the cardiac valve fixing device according to an embodiment of the present invention.

FIG. 14 is a diagram showing a state in which the cardiac valve fixing device of FIG. 1 fixes the mitral valve.

FIG. 15 is a diagram showing a state in which the cardiac valve fixing device of FIG. 1 fixes a tricuspid valve.

FIG. 16 is a real view of a first modified example of the cardiac valve fixing device of FIG. 1.

FIG. 17 is a real view showing a side surface of FIG. 16.

FIG. 18 is a real view of a second modified example of the cardiac valve fixing device of FIG. 1.

FIG. 19 is a real view showing a side surface of FIG. 18.

FIG. 20 is a real view of a third modified example of a cardiac valve fixing device of FIG. 1.

FIG. 21 is a real view showing a side surface of FIG. 20.

FIG. 22 is a real view of a fourth modified example of the cardiac valve fixing device of FIG. 1.

FIG. 23 is a real view showing a side surface of FIG. 22.

BEST MODE FOR THE INVENTION

Exemplary embodiments of the present invention will be described below in more detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Throughout the disclosure, like reference numerals refer to like parts throughout the various FIG. s and embodiments of the present invention.

Hereinafter, a preferred embodiment of the present invention by which an object of the present invention can be concretely realized will be described with reference to the accompanying drawings. In describing the present embodiment, the same configurations are used as the same names and the same reference numerals, and the additional description thereof will be omitted.

A cardiac valve fixing device according to the present invention is a device that is inserted into a body of a target user to fix a specific site, and the device may be formed in the form of a general stent, and alternatively, it can be formed in another form.

Various embodiments of the present invention will be described below referring to the drawings.

First, a schematic configuration and form of the cardiac valve fixing device according to an embodiment of the present invention will be descried referring to FIGS. 1 to 5.

FIG. 1 is a perspective view schematically showing a configuration of a first structure 100 in the cardiac valve fixing device according to an embodiment of the present invention. FIG. 2 is a perspective view schematically showing a construction of a second structure 200 in the cardiac valve fixing device according to an embodiment of the present invention.

Further, FIG. 3 is a diagram showing a state in which the first structure 100 and the second structure 200 are coupled to each other in the cardiac valve fixing device according to an embodiment of the present invention. FIG. 4 is a real view of the cardiac valve fixing device of FIG. 3. FIG. 5 is a real view showing a side surface of FIG. 4.

The cardiac valve fixing device according to the present invention is a device that is inserted into the inside of the body of the target user using a separate insertion device 10 by a user, and specifically, a device that fixes the cardiac valve after penetration into the inside of the target user's heart through the insertion device 10.

As shown in FIGS. 1 to 5, the cardiac valve fixing device according to the present invention generally includes a first structure 100, a second structure 200 and a fixing barb 300.

The first structure 100 is formed of a flexible material to continuously come into contact with the lower surface of the cardiac valve.

The first structure 100 is formed of a flexible material to come into contact with the lower surfaces of the pair of the cardiac valves. Specifically, in this embodiment, the first structure 100 is configured to have a predetermined periphery and continuously come into contact with the lower surfaces of the pair of the cardiac valves, and the first structure 100 includes a first protruding portion 120 formed to protrude outward from the center, and a first recessed portion 110 that is continuously connected to the first protruding portion 120 to form the periphery and is recessed at the center.

Further, the first protruding portion 120 and the first recessed portion 110 are continuously repeated along the periphery and are radially formed, and one surfaces thereof are formed to come into contact with the cardiac valve.

That is, the first structure 100 is made of a material similar to a flexible wire to form a periphery, continuously forms the first protruding portion 120 and the first recessed portion 110, and each of the first protruding portion 120 and the first recessed portion 110 is configured to be radially arranged. In this way, since the first structure 100 is radially formed by continuous arrangement of the first protruding portion 120 and the second protruding portion 220, a contact area with the cardiac valve increases.

Furthermore, in the first structure 100, since a valve muscle fiber (M: see FIG. 11) configured to support and move the cardiac valve is located in the portion of the first recessed portion 110 to secure a space, interference between the first structure 100 and the valve muscle fiber M does not occur.

The second structure 200 is formed similarly to the first structure 100 as described above and is flexibly formed. The second structure 200 comes into contact with the upper surface of the cardiac valve to fix the cardiac valve, together with the first structure.

In this embodiment, the second structure 200 includes a second protruding portion 220 that is spaced apart from the first structure 100, is connected thereto in a lamination form with a predetermined distance, and is formed to protrude outward from the center at a predetermined circumferential, and a second recessed portion 210 which is continuously connected to the second protruding portion 220 to form the periphery and is recessed at the center. Further, the second protruding portion 220 and the second recessed portion 210 are continuously repeated along the periphery and are radially formed, and one surfaces thereof are configured to come into contact with the cardiac valve.

Here, the second structure 200 is made of a flexible material, similarly to the first wire described above, successively forms the second protruding portion 220 and the second recessed portion 210, and each of them is configured to be radially disposed. Thus, the second protruding portion 220 and a second recessed portion 210 are continuously formed in the second structure 200 and the length of the periphery increases, whereby, the contact area with the cardiac valve increases.

At this time, the second structure 200 is formed in the same form as the first structure 100 or alternately, the first and second structures can be formed in different forms from each other.

Thus, the first structure 100 and the second structure 200 are disposed so as to face each other and come into contact with each other at the top and the bottom of the pair of the cardiac valves to support the cardiac valves. Further, as the first structure 100 and the second structure 200 are radially formed as shown, the periphery increases, an area with the cardiac valve increases, and thus, the cardiac valve can be stably fixed.

The fixing barb 300 is provided on at least one of the first structure 100 or the second structure 200, and one or more fixing barbs are formed to protrude in the direction of the cardiac valve and are inserted into the cardiac valves. Further, the fixing barb 300 is located in a space in which the first structure and the 100 and the second structure 200 are arranged in a laminated form.

Specifically, the fixing barb 300 is thinly formed and is placed at the outside along the periphery of the first structure 100 or the second structure 200, and the fixing barb 300 is formed so that first structure 100 or the second structure 200 protrude in directions facing each other. In this way, when the first structure 100 and the second structure 200 come into contact with the upper and lower surfaces of the cardiac valves as the fixing barb 300 is located at the outside along the periphery, the first structure 100 and the second structure 200 can be inserted into the cardiac valve to stably come into contact with the cardiac valve.

More specifically, considering the fixing barb 300 according to the present embodiment, the fixing barb 300 is disposed to protrude only from a part of each of the first protruding portion 120 and the second protruding portion 220. That is, the fixing barb 300 is located at the outside along the periphery of the first structure 100 and the second structure 200, and is configured to be inserted into the cardiac valve.

In this embodiment, the first protruding portion 120 and the second protruding portions 220 are disposed to intersect with each other, and the fixing barb 300 may be disposed only in one of the first protruding portion 120 or the second protruding portion 220.

Meanwhile, unlike the illustrated configuration, the first structure 100 and the second structure 200 may be formed in the same shape and may be disposed to face each other. That is, the first recessed portion 110 and the second recessed portion 210 may be disposed to face each other.

Here, the fixing barb 300 may be formed only in one at the facing point of the first structure 100 and the second structure 200, and when the fixing barb 300 is provided in the first protruding portion 120, the fixing barb 300 may be fixed to the second protruding portion 220 through the cardiac valve.

The cardiac valve fixing device according to the present invention may further include a separate connecting portion 400 that connects the first structure 100 and the second structure 200. Specifically, the connecting portion 400 in this embodiment is disposed between the first structure and 100 and the second structure 200, has a periphery having a relatively small size, and connects the first structure 100 and the second structure 200.

As illustrated, the connecting portion 400 is made of a wire of a flexible material to interconnect the first structure 100 and the second structure 200, and maintains an interval so that the first structure 100 and that the second structure 200 are disposed to be spaced apart from each other. Here, the connecting portion 400 has an outer diameter formed to be relatively smaller than the first structure 100 and the second structure 200, and is located in a fixed site of the cardiac valve upon treatment to the cardiac valves.

In this way, since the heat valve fixing device according to the present invention is provided with the connecting portion 400, the first structure 100 and the second structure 200 are stably connected to each other, and it is possible to ensure a deployment time of the first structure 100 and the second structure 200 during treatment. This is a configuration that can be essentially used in the process of making a structure in the form of common stent.

As mentioned above, the cardiac valve fixing device according to an embodiment of the invention is configured to include the first structure 100 and the second structure 200 that come into contact with the upper and lower surfaces of the cardiac valve, the connecting portion 400 configured to connect the first and second structures, and the fixing barb 300 that is inserted into the cardiac valve to allow the first structure 100 and the second structure 200 to stably come into contact with each other.

Next, referring to FIGS. 6 to 10, a state in which the cardiac valve fixing device according to an embodiment of the present invention 10 forms a shape by a separate insertion device in stages will be described as follows.

FIGS. 6 to 8 are diagrams showing a state in which the first structure 100 in the cardiac valve fixing device of FIG. 1 is exposed, while having shape by a separate insertion device 10. FIGS. 9 and 10 are diagrams showing a state in which the second structure (200) in the cardiac valve fixing device of FIG. 5 is exposed, while having shape by the insertion device (10).

First, referring to FIGS. 6 to 8, the cardiac valve fixing device is inserted into the inside of the heart, by the insertion device 10 that has an insertion tube 12 formed long with a free space inside, and an internal tube 14 that moves at the inside of the insertion tube 12 to expose the cardiac valve fixing device 12 to the outside of the insertion tube 12.

More specifically, the cardiac valve fixing device is provided at the inside of the insertion tube 12 of the insertion device 10, and as shown, the cardiac valve fixing device provided at the inside of the insertion tube 12 is partially exposed to the right end portion.

Here, the cardiac valve fixing device is configured so that the first structure 100 is exposed through the right side of the insertion tube 12. At this time, the cardiac valve fixing device is exposed to the outside of the insertion tube 12 by movement of the inner tube 14, and only the portion of the first structure 100 is exposed. Further, in the exposed first structure 100, the fixing barb 300 protruding in the direction of the insertion tube 12 is exposed together.

That is, as shown in FIGS. 6 to 8, when the first structure 100 is exposed to the outside of the insertion tube 12, since it is divided from the second structure 200 in the connecting portion 400, only the first structure 100 is exposed and bent, and the first structure 100 provided in the insertion tube 12 is unfolded by the elasticity as it is exposed to the outside.

Next, when considering FIGS. 9 and 10, as a continuous process as that in FIG. 8, FIGS. 9 and 10 show a state in which, after the first structure 100 is exposed to the outside, the second structure 200 is exposed. As illustrated, the second structure 200 is in a state of being connected to the first structure 100 by the connecting portion 400, and the second structure 200 is exposed to the right of the insertion tube 12.

At this time, since the exposed second structure 200 is formed of a flexible wire, although it is disposed in the folded state at the inside of the insertion tube 12, the second structure 200 is unfolded when being exposed to the outside of the insertion tube 12 by movement of the inner tube 14.

In this way, as the second structure 200 is exposed to the outside of the insertion tube 12, it is disposed in a laminated form together with the already exposed first structure 100, and the fixing barb 300 provided in the second structure 200 is disposed to protrude to the right.

That is, the first structure 100 and the second structure 200 are disposed in the laminated form each other, and the fixing barbs 300 provided in each of them are disposed so as to protrude toward each other.

Thus, when each of the first structure 100 and the second structure 200 comes into contact with the upper and lower surfaces of the cardiac valve, the fixing barbs 300 are inserted into the cardiac valves, and thus, each of the first structure 100 and the second structure 200 stably comes into contact with the cardiac valves.

The cardiac valve fixing device can stably come into contact with the cardiac valve to fix the cardiac valve through such a process.

Next, referring to FIGS. 11 to 14, the process of treatment of the cardiac valve fixing device according to the embodiments of the present invention to a target user by the insertion device 10 will be described as follows.

FIG. 11 is a perspective view showing a state in which the cardiac valve fixing device according to the embodiment of the present invention is moved to the inside of the heart by the separate insertion device 10, and as illustrated, the insertion tube 12 is inserted into the heart to be the target user. At this time, the insertion tube 12 is located so as to penetrate through the pair of the cardiac valves. In this embodiment, the cardiac valve fixed by the insertion tube will be described as a mitral valve V located between a left atrium and a left ventricle.

More specifically, after the distal end of the insertion tube 12 is inserted through the right atrium, it moves to the left atrium through an interauricular septum, and is located between the mitral valves V within the left atrium.

In this way, by inserting the insertion tube 12 into the inside of the heart, the cardiac valve fixing device provided at the inside of the insertion tube 12 can be exposed to the outside.

FIG. 12 shows a state in which the first structure 100 is in contact with the lower surface of the mitral valve V in the cardiac valve fixing device according to an embodiment of the present invention.

As shown in FIG. 12, the first structure 100 exposed to the outside of the insertion tube 12 through the tip of the insertion tube 12 continuously comes into contact with the lower surface of the mitral valve V. Specifically, the first structure 100 exposed from the insertion tube 12 penetrates through the pair of the mitral valves V to bring the first structure 100 into contact with a point to be exposed at the bottom. At this time, the fixing barb 300 provided in the first structure 100 can be inserted into the mitral valve V, and as the fixing barb 300 is inserted into the mitral valve V, the first structure 100 stably comes into contact with the lower contact of the mitral valve V.

Here, the first structure 100 is disposed so that valve muscle fibers M connect to the mitral vale V is located at the formed first recessed portion 110 to prevent interference and with the valve muscle fibers M.

FIG. 13 shows a state in which the second structure 200 is in contact with the upper surface of the mitral valve V in the cardiac valve fixing device according to an embodiment of the present invention.

As shown in FIG. 13, first, after the first structure 100 exposed to the outside of the insertion tube 12 is brought into contact with the lower surface of the mitral valve V, and the second structure 200 left at the inside of the insertion tube 12 is exposed to the outside again. At this time, the second structure 200 located at the inside of the insertion tube 12 is exposed to the outside at the top of the pair of mitral valve V.

In this way, as the second structure 200 is exposed, the second structure 200 comes into contact with the upper surface of the mitral valve V, and thus, the second structure 200 and the first structural member 100 come into contact with each of the upper and lower surfaces of the mitral valve V to fix the mitral valve V.

In this embodiment, the fixing barb 300 provided in the second structure 200 protrudes downward and is inserted into the mitral valve V, and as the fixing barb 300 is inserted in this way, the second structure 200 stably comes into contact with the upper surface of the mitral valve V.

When considering the state after the cardiac valve fixing device is operated to the heart of the target user, the second structure 200 comes into contact with the top of the pair of mitral valves V, the first structure comes into contact with the bottom, and the connecting portion 400 is provided between the first structure 100 and the second structure 200 such that the first structure 100 and the second structure body 200 are connected to each other in a laminated form.

The process of inserting the cardiac valve fixing device through the insertion device 10 has been described, and the state in which the cardiac valve fixing device is coupled to the mitral valve V becomes a shape as illustrated in FIG. 14. That is, when the cardiac valve fixing device is inserted, as shown in FIG. 14, a state in which a part of the mitral valve V is fixed and is in contact is obtained, and the remaining portions are moved so that the atriums and ventricles are continuously and selectively closed.

Unlike the configuration described above, the cardiac valve fixing device according to the present invention can also be applied to a tricuspid valve film located between the right atrium and right ventricle as shown in FIG. 15, and can be applied also to fixation of the aortic valve film and pulmonary valve film, as well as the mitral valve V.

Next, referring to FIGS. 16 to 23, various modified examples of the cardiac valve fixing device according to an embodiment of the present invention will be described as follows.

FIGS. 16 to 23 are real views showing a first modified example to a fourth modified example of the cardiac valve fixing device of FIG. 1.

When considering the illustrated drawings, various forms of the first structure 100 and the second structure 200 are formed, and a fixing barb 300 is formed in each of them in a direction facing each other.

In this way, since the cardiac valve fixing device is formed in various shapes, it is possible to operate the cardiac valve fixed devices of various forms depending on the shape, sizes and states of the cardiac valves of the target users. In particular, it is possible to use a type having small size of protruding portions 120, 220 and depressed portions 110, 210 in case of a child with a small size of heat, and other forms can be applied, depending on the type of the cardiac valves.

That is, as shown in the examples of the present invention, as long as the first structure 100 and the second structure 200 are provided with the fixing barbs 300 and are configured to be able to fix the cardiac valve, various forms of the first structure 100 or the second structure 200 can be applied. Of course, as described above, likewise, the forms of the first structure 100 and the second structure 200 may also be formed to be different from each other.

As described above, preferred embodiments of the present invention have been described, and it will be apparent to those having ordinary skill in the art that, in addition to the embodiments described above, the present invention can be embodied in other specific forms without departing from its spirit and categories. Therefore, the above embodiments should to be regarded as being illustrative rather than being restrictive, and accordingly, the present invention is not limited to the above description and can also be modified within categories of the appended claims and their equivalent scope.

The invention claimed is:

1. A cardiac valve fixing device comprising:
   a first structure configured in size and shape to, when deployed, continuously contact lower surfaces of leaflet tissue of a targeted cardiac valve;
   a second structure connected to the first structure and configured in size and shape to, when deployed, continuously contact upper surfaces of the leaflet tissue of the targeted cardiac valve, the first structure and second structure thereby grasping the leaflet tissue of the targeted cardiac valve therebetween; and
   a fixing barb that is provided in at least one of the first structure or the second structure, the fixing barb being formed to protrude, when the device is deployed, toward and into the grasped leaflet tissue, wherein the fixing barb is formed on an outside along a periphery of the first structure or the second structure.

2. The cardiac valve fixing device of claim 1, wherein the first structure has a predetermined periphery, and a part along the periphery is formed with a first recessed portion recessed inward.

3. The cardiac valve fixing device of claim 1, wherein the second structure has a predetermined periphery, and a part along the periphery is formed with a second recessed portion recessed inward.

4. The cardiac valve fixing device of claim 1, wherein the first structure has a predetermined periphery, and a part along the periphery is formed with a first recessed portion recessed inward, the second structure has a predetermined periphery, and a part along the periphery is formed with a second recessed portion recessed inward, and the first recessed portion and the second recessed portion are disposed to intersect with each other.

5. The cardiac valve fixing device of claim 1, wherein the fixing barb is formed only in one of mutually facing points of the first structure and the second structure.

6. The cardiac valve fixing device of claim 1, wherein the second structure is formed to have a shape different from the first structure.

7. The cardiac valve fixing device of claim 1, further comprising:
   a connecting portion that is disposed between the first structure and the second structure, has a periphery of a relatively small size, and connects the first structure and the second structure.

8. The cardiac valve fixing device of claim 1, wherein the device is configured such that, when deployed, grasped leaflet tissue remains a functional part of the targeted cardiac valve.

9. The cardiac valve fixing device of claim 1, wherein the device has a lateral width such that, when deployed at the targeted cardiac valve, the device allows for blood flow around the device and through the targeted cardiac valve.

10. The cardiac valve fixing device of claim 1, wherein the device is configured in size and shape such that when deployed the device does not interfere with tendineae of the targeted cardiac valve.

11. A cardiac valve fixing device configured for grasping cardiac valve leaflet tissue, the device comprising:
    an upper section configured to engage against an upper side of leaflet tissue of a targeted cardiac valve when the device is deployed, the upper section having a periphery;
    a lower section connected to the upper section and configured to engage against a lower side of the leaflet tissue of the targeted cardiac valve when the device is deployed, the lower section having a periphery; and
    a plurality of barbs disposed along the periphery of the upper section and/or the periphery of the lower section, each barb extending toward an opposite section so as to extend into leaflet tissue grasped between the upper and lower sections,
    wherein the periphery of the upper section includes one or more recessed portions recessed radially inward and one or more protruding portions extending radially outward, and wherein the periphery of the lower section includes one or more recessed portions recessed radially inward and one or more protruding portions extending radially outward.

12. The cardiac valve fixing device of claim 11, wherein the upper section and lower section are oriented relative to one another such that the one or more protruding portions of the upper section are offset from the one or more protruding portions of the lower section.

13. The cardiac valve fixing device of claim 11, wherein each of the barbs extend from a protruding portion of the upper section or protruding portion of the lower section.

14. The cardiac valve fixing device of claim 11, wherein both the upper section and the lower section include barbs.

15. A cardiac valve fixing device comprising:
- a first structure configured in size and shape to, when deployed, continuously contact lower surfaces of leaflet tissue of a targeted cardiac valve;
- a second structure connected to the first structure and configured in size and shape to, when deployed, continuously contact upper surfaces of the leaflet tissue of the targeted cardiac valve, the first structure and second structure thereby grasping the leaflet tissue of the targeted cardiac valve therebetween; and
- a fixing barb that is provided in at least one of the first structure or the second structure, the fixing barb being formed to protrude, when the device is deployed, toward and into the grasped leaflet tissue,
- wherein the first structure has a predetermined periphery, and a part along the periphery is formed with a first recessed portion recessed inward, the second structure has a predetermined periphery, and a part along the periphery is formed with a second recessed portion recessed inward, and the first recessed portion and the second recessed portion are disposed to intersect with each other.

* * * * *